United States Patent [19]

Shen

[11] Patent Number: 4,626,251
[45] Date of Patent: Dec. 2, 1986

[54] SURGICAL SPONGE
[76] Inventor: Albert Shen, 7 Annabelle La., Florham Park, N.J. 07932
[21] Appl. No.: 704,616
[22] Filed: Feb. 22, 1985
[51] Int. Cl.[4] ............................................. A61F 13/00
[52] U.S. Cl. ................................................... 604/362
[58] Field of Search ........................................ 604/362

[56] References Cited

U.S. PATENT DOCUMENTS

| 3,097,649 | 6/1963 | Gray | 604/362 |
|---|---|---|---|
| 3,133,538 | 5/1964 | Pratt et al. | 604/362 |
| 3,698,393 | 10/1972 | Stone | 604/362 |
| 3,756,241 | 9/1973 | Patience | 604/362 |
| 4,068,666 | 1/1978 | Schiff | 604/362 |
| 4,540,398 | 9/1985 | Barson et al. | 604/362 |

FOREIGN PATENT DOCUMENTS 0948387 6/1974 Canada .................... 604/362

Primary Examiner—Dalton L. Truluck
Assistant Examiner—Karen L. Kaechele
Attorney, Agent, or Firm—Bruce M. Collins

[57] ABSTRACT

A radiopaque tell-tale filament is disposed between two plies of a multi-ply surgical sponge in the quadrangular area defined by the stitched or folded edges of the sponge and an inwardly disposed continuous stitch. The ends of the tell-tale are embedded in the stitching but the intermediate portion of the filament is otherwise freely disposed in the quadrangular area.

6 Claims, 3 Drawing Figures

SURGICAL SPONGE

DETAILED DESCRIPTION

Surgical sponges such as laparotomy sponges are commonly fabricated with a radiopaque tell-tale which permits an X-ray determination of whether or not such a sponge inadvertently may have been left inside a body cavity in the course of an operation. The underlying problem and proposed solutions are fully described for example by Patience in U.S. Pat. No. 3,756,241.

In order to insure that the tell-tale is prominent on an X-ray, a radiopaque strip of substantial width, such as that disclosed in U.S. Pat. No. 4,068,666 to Shiff, often is employed. Because of the possibility of such a strip being masked by a bone, and the further possibility that the strip may be oriented within the body cavity so that only its relatively linear cross-section is visible in the X-ray, the use of various elongated radiopaque tell-tales has been suggested. Typical elongated tell-tales are the radiopaque filaments such as described by Walters et al. in U.S. Pat. No. 3,508,551, including those which are disposed in a characteristic pattern as in Pratt et al., U.S. Pat. No. 3,133,538, and elongated radiopaque elements of varying thickness as in Hardy et al., U.S. Pat. No. 3,965,907.

The incorporation of such elongated radiopaque tell-tales generally involves some form of thermoplastic adhesion by which the filament fiber threads or element is anchored to the surgical sponge. It is necessary of course that any tell-tale introduced into such a surgical sponge be firmly connected to the sponge so that the tell-tale itself does not break or become dislodged in the course of the operation and remain behind in the body cavity (even though the sponge itself is removed). Such thermoplastic adhesion, while necessary, adds to the cost of production of the final product and in some cases increases the number of production steps. Moreover, and as discussed by Shiff, U.S. Pat. No. 4,068,666, it is common practice for hospitals to launder such sponges prior to their use. This softens the pad, rendering it less traumatic, and increases the absorbency and fluffiness of the sponge but also increases the risk of such thermoplastic threads becoming dislodged in the course of such laundering.

The present invention pertains to a surgical sponge of the type described which is easily and economically constructed and provides the advantages associated with a radiopaque tell-tale of the filament type but without the attendant disadvantages of the prior art devices.

Referring to the drawings.

Figure 1:
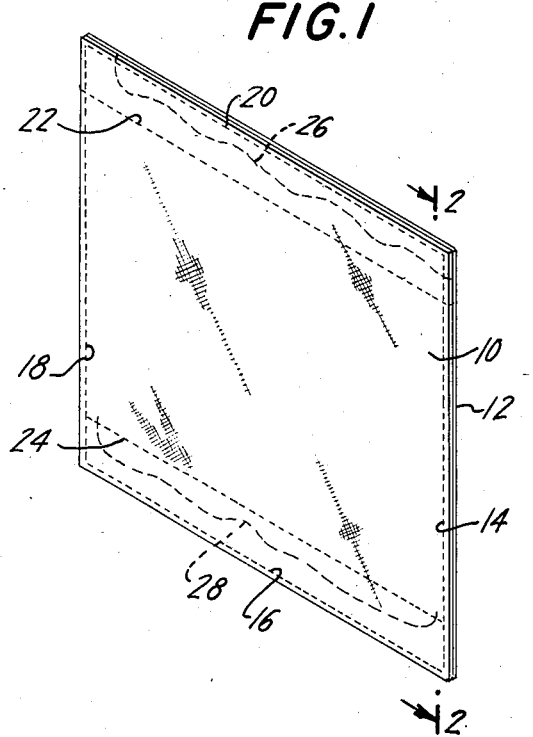
FIG. 1 is a perspective view of the surgical sponge according to the present invention.
Figure 2:
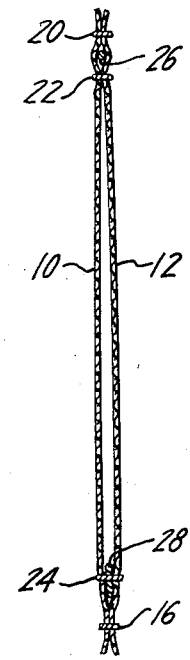
FIG. 2 is a cross-section of the sponge shown in FIG. 1 taken along line 2—2.

Referring now in greater detail to the drawings, the surgical sponge is constructed from a plurality of plies of absorbent material 10 and 12. The absorbent material may be any of the hydrophilic materials commonly used for this purpose, as for example conventional gauze. The edges of the sponge are sealed by stitching 14, 16, 18, and 20 disposed along the sponge's perimeter and through the individual plies of the sponge. Alternatively as is shown in FIG. 3, an edge of the sponge may be sealed by a fold 40 in the absorbent material so that one ply defines at least two plies of the sponge.

In addition to stitching 14, 16, 18, and 20 about the perimeter of the sponge, there will be at least one continuous stitch disposed inwardly from and relatively parallel to at least one of the sealed edges. In the embodiment shown in FIG. 1, stitch 22 is disposed inwardly from and roughly parallel to the edge of the sponge defined by perimeter stitching 20, and stitching 24 is disposed inwardly from and roughly parallel to the edge of the sponge defined by perimeter stitching 16. Each of such inwardly disposed stitching thereby defines a roughly quadrangular area which is bound by the first sealed edge 16 and 20, the inwardly disposed stitching 22 and 24, respectively and portions of the two adjoining and transverse sealed edges 14 and 18. It will be appreciated that such area is only roughly quadrangular since the stitching need not be, and generally will not be, entirely linear nor exactly parallel. In addition, it is often desirable to apply such stitching in a plurality of more or less superimposed passes which however are applied to a general area without a need for a high degree of accuracy.

Disposed within the quadrangular area just defined, and lying between two plies of the sponge, is one or more radiopaque threads or filaments 26 and 28 which constitute the tell-tale. Each end of the radiopaque thread is embedded in stitching which defines the side or sides of the quadrangular area. The two points of attachment for the filament ideally should be widely separated from one another in order to maximize the length over which the radiopaque thread is disposed. Between the two points of attachment, however, the radiopaque thread is freely disposed within the quadrangular area and otherwise unbound to the sponge. Consequently, and because the tell-tale does not rely upon other means of adhesion, being attached in the course of stitching, and is protected by the plies of the sponge but free from any stress over its length, it is virtually impossible for the tell-tale to become dislodged (short of a total breakdown of the sponge or its stitching).

Figure 3:
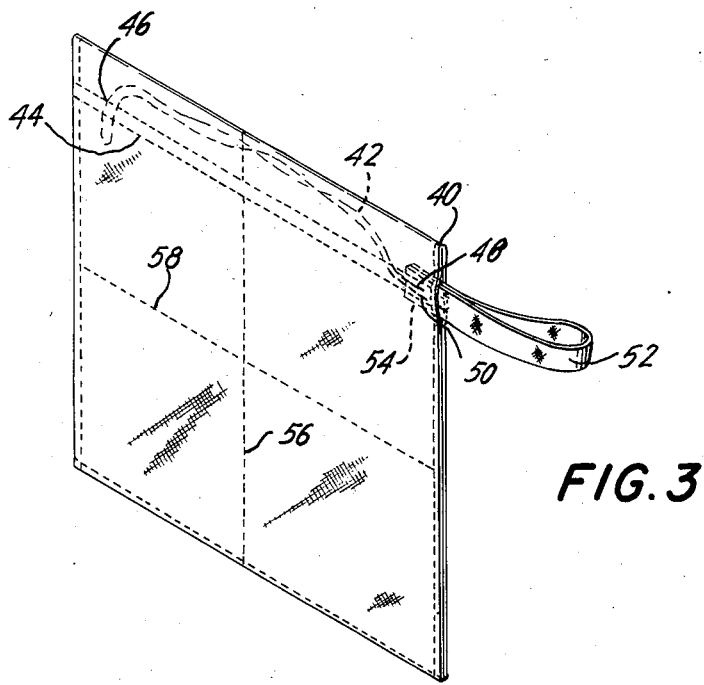
FIG. 3 is a perspective view of a second embodiment according to the present invention.

In the embodiment shown in FIG. 3, the radiopaque thread 42 is double-backed on itself so as to form a double strand with the general portion of the thread at which the double-backing occurs being embedded in the stitching 44 at a first point 46 and the two free ends 48 and 50 being embedded at a second point 54. More than one double strand, for example two or three, can be used, providing in the example given four or six individual strands.

The radiopaque thread can be embedded in any of the stitching(s) which defines the quadrangular area including that defining the edge of the sponge (as for examples edges 14 and 20 in the case of thread 26 in FIG. 1), the inwardly disposed stitching (as for example stitching 24 in the case of radiopaque thread 28 in FIG. 1), or any combination thereof. Preferably, the radiopaque thread is embedded at at least one point in the inwardly disposed stitching since this prevents any portion of the radiopaque thread from extending beyond the perimeter of the sponge.

In the embodiment shown in FIG. 3, the surgical sponge is provided with a loop or handle 52 which is conventional in this type of sponge. For ease of fabrication, it is desirable that this loop, which is stitched to but extends beyond the edge of the sponge, be positioned so as to constitute one of the points of attachment for the radiopaque thread. Hence radiopaque thread 42 is embedded in the stitching at a first point 46 and at a second point 54 which coincides with the stitching utilized to attach loop 52. In a preferred embodiment, second point 54 lies on the inwardly disposed stitching which stitching thereby also serves to attach loop 52.

Supplemental stitching 56 and 58 can also be provided to further secure the plurality of plies of absorbent material but are not required with respect to the anchoring of the radiopaque thread.

One of the advantages of the present surgical sponge is its ease of fabrication. Hence the radiopaque thread need only be placed between the plies in a general orientation and its two ends sealed in the course of stitching as discussed above. In an embodiment shown in FIG. 3, the absorbent material is folded along fold 40 with the thread placed between the thus-created two plies. Loop 52 is similarly inserted, and the stitching defining the three remaining edges and the inwardly disposed stitching then is applied. The resultant surgical sponge can then be laundered prior to use without fear of dislodging the radiopaque tell-tale and used in the surgical procedures with the same assurance.

What is claimed is:

1. A surgical sponge having a plurality of plies of absorbent material, each edge of the sponge being sealed either by a fold in said material which thereby defines two plies or by stitching joining the edge of each ply to the corresponding edge of each contiguous ply,
    at least one continuous stitch through said plies being disposed inwardly from and roughly paralllel to a first of said sealed edges so as to define, together with second and third adjoining transverse sealed edges, a roughly quadrangular area, and
    at least one radiopaque thread disposed within said quadrangular area between two plies of said sponge, said radiopaque thread being embedded at first and second points in the stitching defining at least one side of said quadrangular area but with the portion of said radiopaque thread between said points being otherwise freely disposed within and unbound to said sponge.

2. A surgical sponge according to claim 1 wherein said radiopaque thread is doubled backed upon itself so as to form a double strand with the portion of the thread at which said double backing occurs being embedded at said first point in said stitching and the two free ends of the thread being embedded at said second point in said stitching.

3. A surgical sponge according to claim 1 wherein said absorbent material is folded so as to define at least two plies of said sponge and said fold constitutes a sealed edge defining one side of said quadrangular area.

4. A surgical sponge according to claim 3 wherein said fold constitutes said first sealed edge and at least one of the points at which said radiopaque thread is embedded lies in said inwardly disposed stitching.

5. A surgical sponge according to claim 4 wherein said radiopaque thread is doubled backed upon itself so as to form a double strand with the portion of the thread at which said double backing occurs being embedded in said inwardly disposed stitching and the two free ends of the thread being embedded in stitching defining an adjoining transverse sealed edge.

6. A surgical sponge according to claim 5 wherein said sponge also comprises a loop stitched to but extending beyond the adjoining transverse edge of said sponge, the two ends of said radiopaque thread being embedded in the stitching defining the adjoining tranverse edge at the same point at which said loop is stitched to said sponge.

* * * * *